United States Patent [19]

Yamamoto et al.

[11] Patent Number: 5,306,645
[45] Date of Patent: Apr. 26, 1994

[54] CONCENTRATION AND TRANSFER METHODS FOR A CHROMATOGRAM AND AN LC/IR MEASURING METHOD

[75] Inventors: Hiroshi Yamamoto, Nagaokakyo; Katsuhiko Ichimura, Kobe; Kenji Nakamura, Ibaraki; Tomiyuki Maeda, Kyoto; Takahiro Tajima, Kyoto; Kiyoshi Wada, Mukaijima-Marumachi, all of Japan

[73] Assignee: Shimadzu Corporation, Kyoto, Japan

[21] Appl. No.: 647,899

[22] Filed: Jan. 30, 1991

[30] Foreign Application Priority Data

Jan. 31, 1990 [JP] Japan .................. 2-23409

[51] Int. Cl.$^5$ .................. G01N 30/94; G01N 30.95
[52] U.S. Cl. .................. 436/162; 73/61.55; 210/198.3; 210/658; 436/161
[58] Field of Search ............ 436/161, 162; 210/658, 210/198.3; 73/61.54, 61.55; 422/56, 57

[56] References Cited

U.S. PATENT DOCUMENTS 3,843,053 10/1974 Thoden .................. 436/162
4,508,624 4/1985 Nagata .................. 210/198.3

FOREIGN PATENT DOCUMENTS 0161351 6/1990 Japan .................. 73/61.55
0280054 11/1990 Japan .

OTHER PUBLICATIONS

Nature; "Quantitative Spot Test on Filter paper and Examples of its Application"; Aug. 6, 1952, vol. 170, pp. 422 Tatsuo Kari Yone.
Beauchemin et al., Quantitative Analysis Of Diazonaphthoquinones By Thin-Layer Chromatographic/Diffuse Reflectance Infrared Fourier Transform Spectrometry, Anal. Chem., 61, 615-618.
Shafer et al., Sample Transfer Accessory For Thin-Layer Chromatography/Fourier Transform Infrared Spectrometry, Anal. Chem., 1986, 58, 2708-2714.
Chalmers et al., Characterization Of Thin-Layer Chromatographically Separated Fractions By Fourier Transform Infrared Diffuse Reflectance Spectrometry, Anal. Chem., 1987, 59, 415-418.

Primary Examiner—James C. Housel
Assistant Examiner—Ramon Torres
Attorney, Agent, or Firm—William L. Klima

[57] ABSTRACT

Methods of conducting Thin Layer Chromatography (TLC) involving using a TLC plate having sample spots and including no support material, placing the TLC plate on a porous substrate, and allowing solvent to move upwardly from the porous substrate toward the TLC plate by capillary action to be vaporized from the surface of the TLC plate, thereby concentrating the sample spots developed in the thin layer on the surface of the TLC plate.

12 Claims, 5 Drawing Sheets

PRIOR ART

CONCENTRATION AND TRANSFER METHODS FOR A CHROMATOGRAM AND AN LC/IR MEASURING METHOD

BACKGROUND OF THE INVENTION

1. Field of the Invention

The present invention relates to a method of concentrating spots which are developed in a plate or paper, generically called a thin-layer chromatography (TLC) plate, for thin-layer chromatography or paper chromatography, and a measuring method for measuring spots which are developed in a TLC plate and sample components which are eluted through liquid chromatography (LC) with an infrared spectrometer such as a Fourier transform infrared (FTIR) spectrometer.

2. Description of the Background Art

A TLC plate for thin-layer chromatography is generally formed by a plate which is prepared by applying silica gel onto a support material such as a glass substrate or an aluminum sheet, while a filter paper is employed for paper chromatography.

FIG. 9 is a sectional view showing a conventional TLC plate for thin-layer chromatography. A silica gel layer 4 is formed on the surface of a glass substrate or aluminum sheet 2. Samples are developed in an in-plane direction of the silica gel layer 4 by an eluant, to define sample spots 6.

The sample spots thus developed in the TLC plate are directly measured with a densitometer, or scraped, extracted and concentrated to be thereafter subjected to spectrometry. However, the method of scraping, extracting and concentrating the spots is incorrect and troublesome.

There has been made an attempt to analyze components which are developed in a TLC plate with an FTIR spectrometer. In order to make analysis with the FTIR spectrometer, there have been proposed a method of directly applying focused infrared light to as-developed spots for measuring diffuse reflectance spectra (refer to Anal. Chem. 1989, 61, pp. 615–618), a method of scraping, extracting, and dripping spot portions on powder pellets of KBr or KCl and drying the same for thereafter measuring the same with an FTIR spectrometer (refer to Anal. Chem. 1987, 59, pp. 415–418), and a method of placing powder having no infrared absorption on an end portion of a TLC plate for transferring spot components from the TLC plate to the powder through glass fibers (refer to Anal. Chem. 1986, 58, pp. 2708–2714).

However, the method of directly applying infrared light to the TLC plate for FTIR measurement is inferior in practicability since silica gel contained in the TLC plate or the paper has large infrared absorption. On the other hand, the method of scraping, extracting, and dripping the component spots on the power pellets of KBr or KCl for FTIR measurement is incorrect and troublesome. In the method of transferring the spot components on the end portion of the TLC plate through the glass fibers, further, resolution in direction of development depends on the pitches of the glass fibers which are provided on the end portion, while this method is applicable only to a one-dimensionally developed TLC plate.

If infrared spectra of components separated through liquid chromatography can be obtained, it is extremely effective as qualitative means. In general, however, an eluant has strong absorption in an infrared region. Thus, it is impracticable to directly measure infrared spectra from an effluent in a flow cell system.

In order to obtain infrared spectra from an effluent in liquid chromatography, it is necessary to remove an eluant from the effluent. Various methods have been proposed for removing such eluants. One of these methods is adapted to drip an effluent on a powder layer of an infrared-nonabsorbent substance, such as KBr or KCl, which is reflective of infrared light, and to vaporize the eluant, thereby performing measurement with an infrared spectrometer. However, this method is impracticable since the powder of the infrared-nonabsorbent substance, such as KBr or KCl, is easily dissolved in water which is contained in the eluant.

Other methods are adapted to drip an effluent on a metal belt, and to spray an effluent onto a metal belt for facilitating vaporization of the eluant. However, these methods are also impracticable due to problems of spreading of spots and low detection sensitivity.

SUMMARY OF THE INVENTION

An object of the present invention is to enable correct and simple measurement with a densitometer as well as spectrometry by directly making concentration on a TLC plate.

Another object of the present invention is to enable correct infrared spectrometry of spot components, which are developed in a TLC plate, by directly transferring the spots onto a layer of an infrared-nonabsorbent substance without scraping the same.

Still another object of the present invention is to provide a method which can measure sample components eluted through liquid chromatography with an infrared spectrometer in high sensitivity while vaporizing an eluant resulting from the liquid chromatography and suppressing spreading of spots.

In a concentration method according to the present invention, a TLC plate having sample spots and including no support material is placed on a porous substrate, and a solvent is upwardly moved from the porous substrate toward the TLC plate by capillary action to be vaporized from the surface of the TLC plate, thereby concentrating the spot samples, developed in the TLC plate, on the surface. When the samples are developed/separated through the TLC plate including no support material and the solvent is moved from a first surface to a second surface of the TLC plate by capillary action, the separated components are concentrated on the second surface.

In a transfer method from a TLC plate to a layer of an infrared-nonabsorbent substance according to the present invention, a TLC plate having sample spots and including no support material is placed on a porous substrate, and a layer of an infrared-nonabsorbent substance is placed on the TLC plate to be in close contact therewith, while a solvent is upwardly moved from the porous substrate toward the infrared-nonabsorbent substance layer through the TLC plate by capillary action to be vaporized from the surface of the infrared-nonabsorbent substance layer, thereby transferring the sample spots which are developed in the TLC plate onto the infrared-nonabsorbent substance layer. When the infrared-nonabsorbent substance layer is brought into contact with one surface of the TLC plate in which the samples are developed/separated and the solvent is moved from another surface of the TLC plate to the surface facing the infrared-nonabsorbent substance layer by capillary action, the separated components are moved and transferred toward the infrared-nonabsorbent substance layer.

In an LC/IR measuring method according to the present invention, an effluent for liquid chromatography is dripped on a porous substrate to vaporize an eluant, and thereafter a layer of infrared-nonabsorbent substance powder is formed on the porous substrate, while a solvent is upwardly moved from the porous substrate toward the infrared-nonabsorbent substance powder layer by capillary action and vaporized from the surface of the infrared-nonabsorbent substance powder layer to transfer the sample components adsorbed by the porous substrate toward the infrared-nonabsorbent substance powder layer, thereby obtaining samples for infrared spectrometry. When the effluent is dripped on the porous substrate to vaporize the eluant, the eluted sample spots are adsorbed by the porous substrate. The infrared-nonabsorbent substance powder layer is formed on the porous substrate, and a transfer solvent is upwardly moved from the porous substrate toward the infrared-nonabsorbent substance powder layer, whereby the sample components adsorbed by the porous substrate are moved and transferred onto the infrared-nonabsorbent substance powder layer.

In order to obtain an IR chromatogram through the LC/IR measuring method, a position of the porous substrate for receiving the effluent for liquid chromatography may be relatively moved at a constant speed with respect to an elution port.

The LC/IR measuring method is employable in various fields utilizing liquid chromatography in relation to organic compounds.

The porous substrate can be formed by a porous ceramic substrate, a porous glass substrate or the like.

The infrared-nonabsorbent substance can be prepared from powder of KBr or KCl, or an alumina ceramic plate.

The solvent for concentrating the sample spots developed in the TLC plate on its surface or transferring the sample components adsorbed by the porous substrate onto the infrared-nonabsorbent substance layer from the porous substrate preferably has high elution power and a low boiling point. If the infrared-nonabsorbent substance layer is made of KBr or KCl, the solvent is prepared from a nonaqueous solvent. Such a solvent can be prepared from methanol, chloroform or the like.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
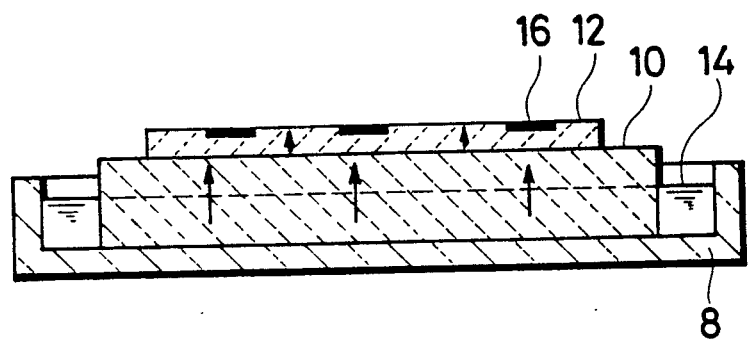
FIG. 1 is a sectional view showing an embodiment of a concentration method according to the present invention.

FIG. 1 shows an embodiment of a concentration method according to the present invention. A porous substrate 10 is placed in a vessel 8, and a TLC plate 12, in which samples are developed, is placed on the porous substrate 10. The TLC plate 12 is formed by a plate for thin-layer chromatography, which includes no support material. Such a TLC plate can be prepared from an Empore (trademark of 3M) TLC sheet (distributed by Analytichem International, Inc.), or a sintered glass plate. Alternatively, the TLC plate 12 may be prepared from a paper for paper chromatography. In this TLC plate 12, the samples have been already developed to define spots. The porous substrate 10 is prepared from a ceramic substrate, or a permeable material such as paper or cloth, for example.

A solvent 14 is introduced into the vessel 8, so that the porous substrate 10 is partially dipped therein. The solvent 14 may be selected from various materials, such as chloroform, for example.

In this state, the solvent 14 is moved toward the surface side through the porous substrate 10 by capillary action, to concentrate the sample spots developed in the TLC plate 12 on its surface side. Numeral 16 denotes the concentrated sample spots.

At this time, the surface of the TLC plate 12 may be fanned to facilitate vaporization of the solvent 14 reaching the said surface, thereby increasing the speed of concentration.

According to this concentration method, the sample spots are concentrated on the surface side of the TLC plate, whereby it is possible to correctly perform measurement with a densitometer, or spectrometry. Further, the concentrating operation is simple.

Figure 2:
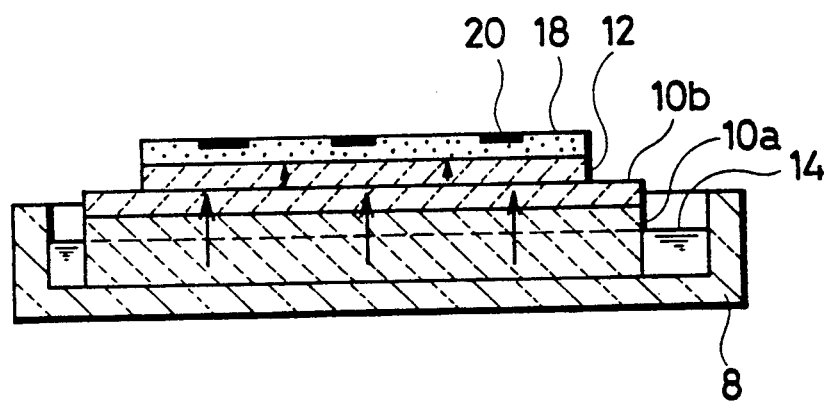
FIG. 2 is a sectional view showing an embodiment of a transfer method according to the present invention.

FIG. 2 shows an embodiment of the inventive method of transferring spot components, which are developed in a TLC plate 12, onto a layer of an infrared-nonabsorbent substance. A pair of ceramic porous substrates 10a and 10b are overlapped and contained in a vessel 8. The upper substrate 10b is detachable from the lower substrate 10a. The TLC plate 12, which includes no support material, is placed on the upper porous substrate 10b. The TLC plate 12 is prepared from an Empore TLC sheet, a sintered glass plate, or a paper for paper chromatography as mentioned above in relation to FIG. 1, for example.

An infrared-nonabsorbent substance layer 18 is formed on the TLC plate 12 in close contact therewith. The infrared-nonabsorbent substance layer 18 is formed of a powdered infrared-nonabsorbent material such as KBr or KCl, or a plate-type material such as an alumina ceramic plate. This infrared-nonabsorbent substance layer 18 is formed on the TLC plate 12, in which samples have been developed to define spots. If the infrared-nonabsorbent substance layer 18 is made of powder and the TLC plate 12 is formed of a flexible material such as an Empore TLC sheet, for example, the TLC plate 12 is first placed on the upper porous substrate 10b and then the powder layer 18 is formed on the TLC plate 12. Thereafter the upper porous substrate 10b is placed on the lower porous substrate 10a, in order to prevent the powder layer 18 from breaking.

A solvent 14 is introduced into the vessel 8 so that the lower porous substrate 10a is partially dipped therein.

In this state, the solvent 14 is passed through the porous substrates 10a and 10b, and upwardly moved through the TLC plate 12 to reach the infrared-nonabsorbent substance layer 18, and vaporized from the surface of the layer 18. Upon such movement of the solvent 14, the sample components developed in the TLC plate 12 are also upwardly moved and transferred onto the infrared-nonabsorbent substance layer 18. Numeral 20 denotes the transferred sample components.

Also in this case, it is effective to fan the infrared-nonabsorbent substance layer 18, in order to facilitate vaporization of the solvent 14 from its surface.

Infrared spectroscopic analysis can be correctly performed after transferring the spot sample components onto the infrared-nonabsorbent substance layer, as shown in FIG. 2. Further, the transfer operation is simple.

Figure 3:
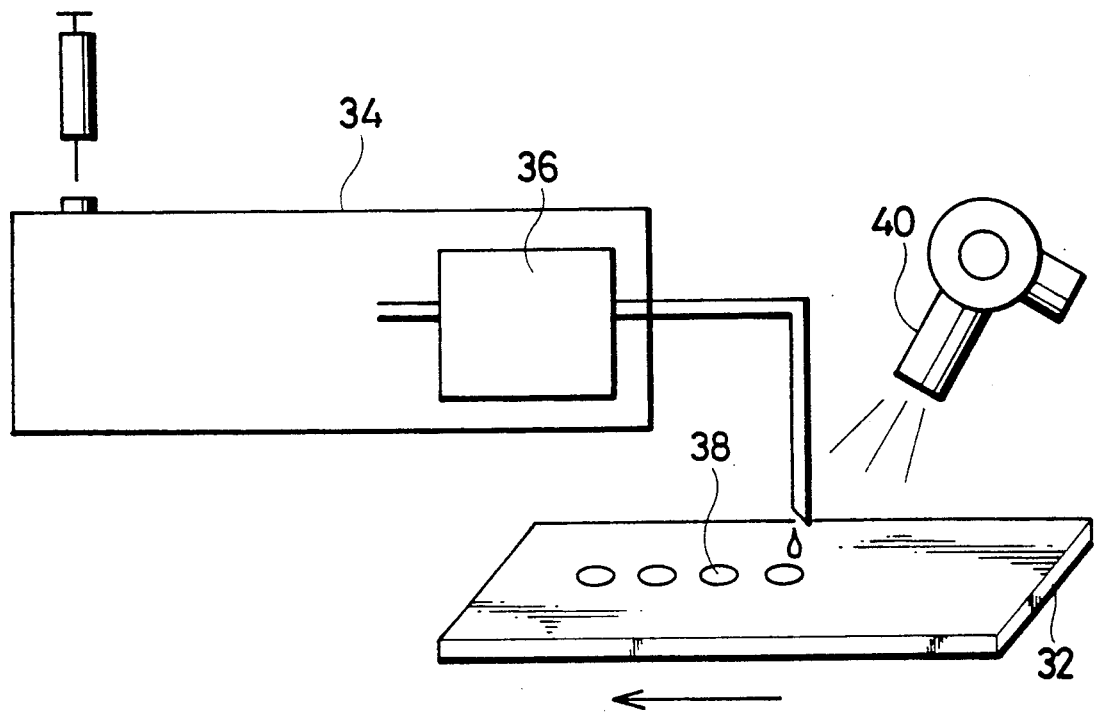
FIG. 3 is a perspective view showing a step of dripping an effluent for liquid chromatography on a ceramic substrate in an embodiment of the present invention.

FIGS. 3 to 6 show a method of preparing samples for infrared spectrometry from an effluent for liquid chromatography. Referring to FIG. 3, numeral 32 denotes a porous ceramic substrate, numeral 34 denotes a high performance liquid chromatograph, and numeral 36 denotes its detector, which is formed by a UV detector, for example. The high performance liquid chromatograph 34 is provided with a column having a small flow rate of tens of microliters per minute, for example. The ceramic substrate 32 is so arranged that its surface is in contact with the forward end of a tube for dripping an effluent passing through the detector 36.

In this state, the ceramic substrate 32 is unidirectionally moved at a constant speed as shown by the arrow, and the effluent dripped thereon is dried with a drying fan 40, thereby vaporizing an eluant. Numeral 38 denotes spots of sample components which are adsorbed by the substrate 32 through such vaporization of the eluant from the effluent. Only the adsorbed sample components are left on the ceramic substrate 32, to form a spatial chromatogram.

Figure 4:
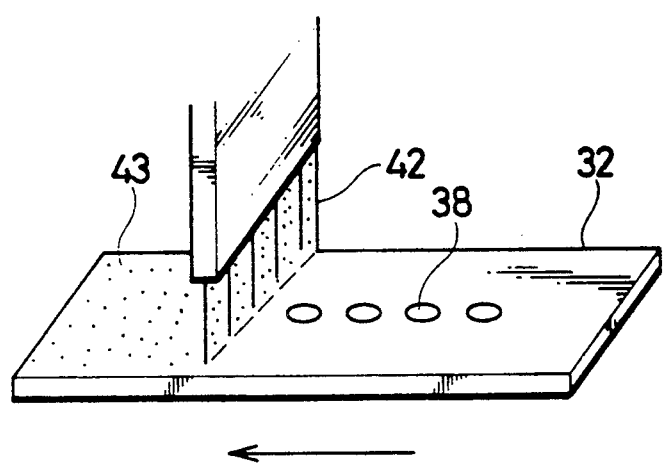
FIG. 4 is a perspective view showing a step of forming a KBr powder layer on the ceramic substrate.

Thereafter KBr powder 42 is uniformly applied onto the ceramic substrate 32 thus having the chromatogram in a small thickness of about 0.5 mm, for example, to form a KBr powder layer 43, as shown in FIG. 4.

Figure 5:
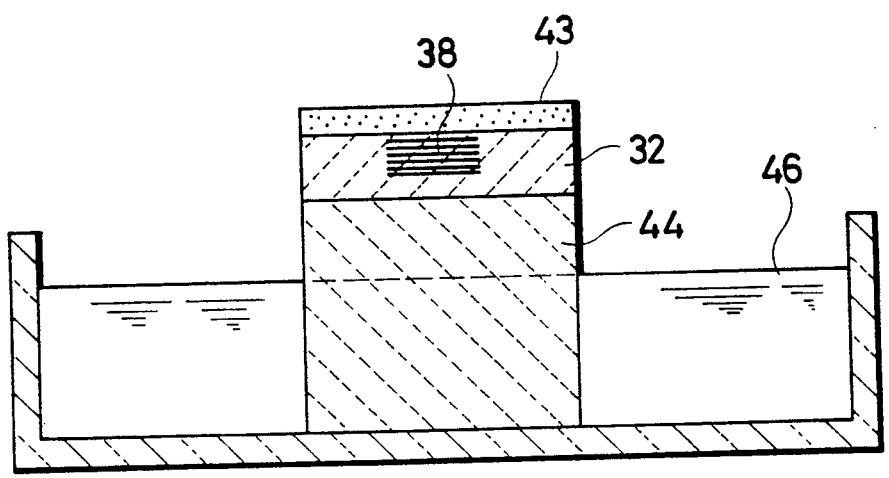
FIG. 5 is a sectional view showing a method of transferring sample components from the ceramic substrate to the KBr powder layer.
Figure 6:
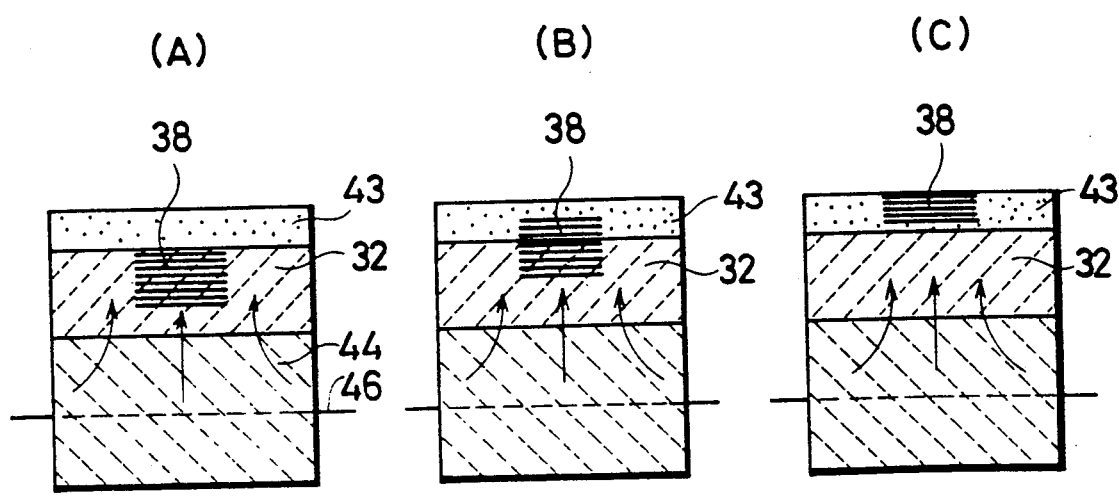
FIGS. 6A-6C are sectional views showing the transfer step.

Then, as shown in FIG. 5, a transfer porous substrate 44 is dipped in a transfer solvent 46, which is prepared from methanol, for example, and contained in a vessel, and the ceramic substrate 32 provided with the KBr layer 43 is placed on the transfer porous substrate 44. The transfer porous substrate 44 is formed by a porous ceramic substrate, for example.

Thus, the solvent 46 is upwardly moved from the transfer porous substrate 44 toward the KBr powder layer 43 through the ceramic substrate 32 by capillary action, and vaporized from the surface of the KBr powder layer 43. During this process, the sample components 38, which have been adsorbed by the ceramic substrate 32, are transferred onto the KBr powder layer 43, as shown at (A), (B) and (C) in FIG. 6.

In such a transfer process, the surface of the KBr powder layer 43 may be fanned with hot air, to facilitate vaporization of the solvent 46.

After a constant period, the ceramic substrate 32 is extracted and dried, to form a chromatogram which has been transferred onto the KBr powder layer 43 and dried.

Figure 7:
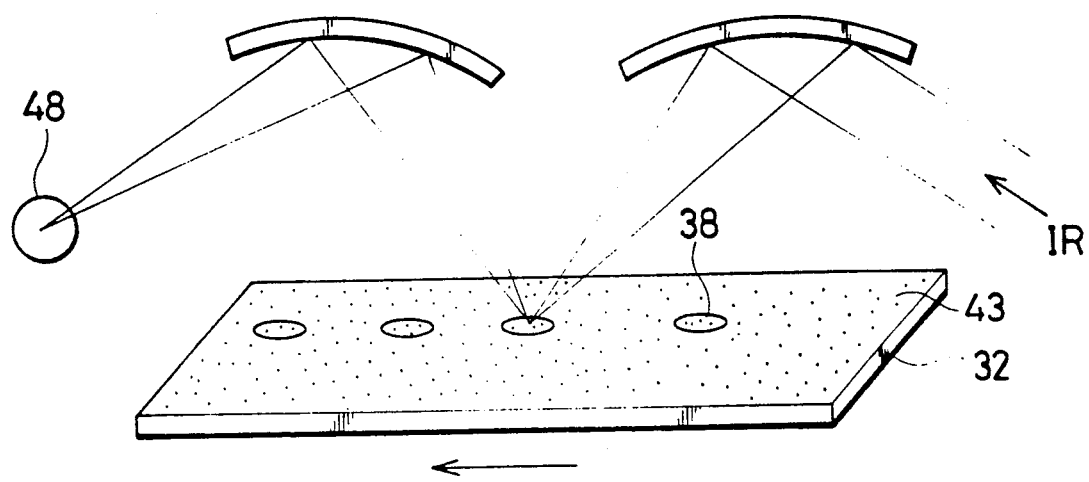
FIG. 7 is a perspective view showing infrared spectrometry through an FTIR diffuse reflectance method.
Figure 9:
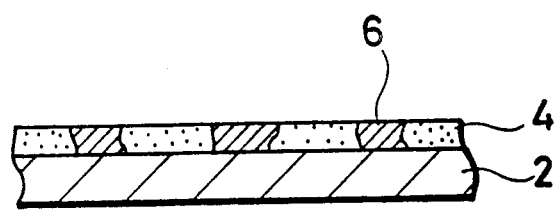
FIG. 9 is a sectional view showing a general TLC plate for thin-layer chromatography.
Figure 8A:
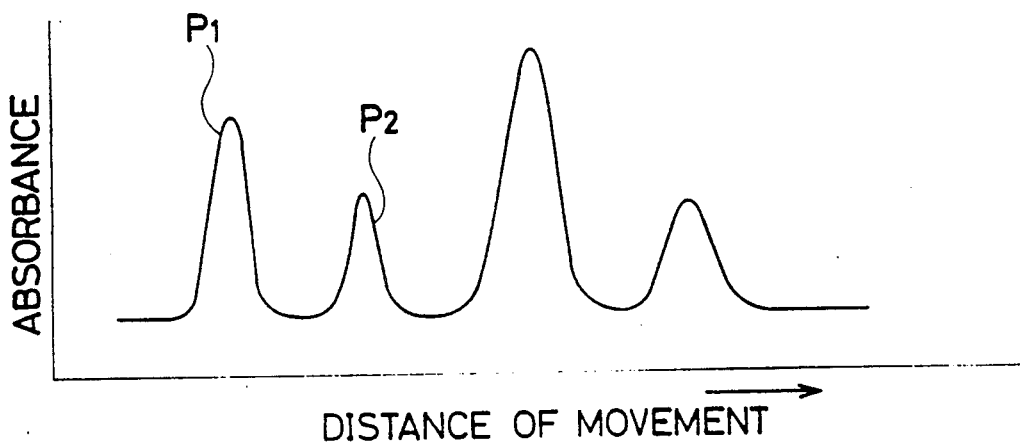
FIG. 8A illustrates an obtained IR chromatogram, and IR spectra of respective peaks at FIGS. 8B and 8C.
Figure 8B:
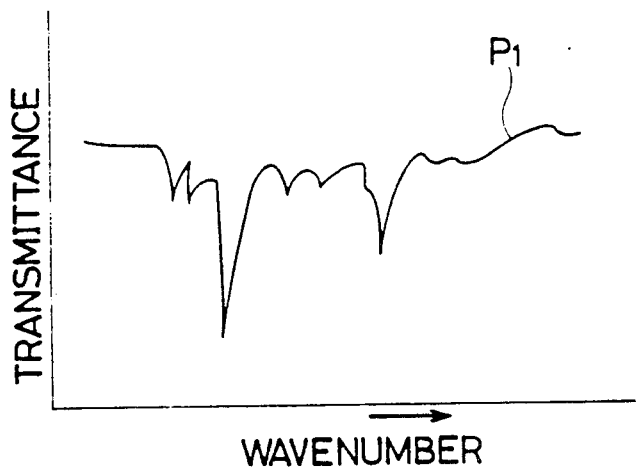
Figure 8C:
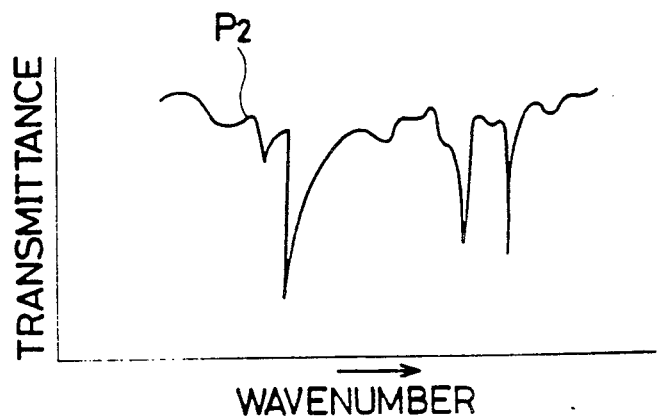

As shown in FIG. 7, the ceramic substrate 32 having the KBr powder layer 43 thereon is moved at a constant speed to measure the as-formed samples for infrared spectrometry through an FTIR diffuse reflectance method. Numeral 48 denotes a detector. FIG. 8 shows the as-formed IR chromatogram at (A), as well as infrared absorption spectra of peaks P1 and P2 in the chromatogram at (B) and (C) respectively. Thus, infrared absorption spectra can be measured simultaneously with measurement of the chromatogram.

In FIG. 3, the ceramic substrate 32 is moved at a constant speed so that the effluent is dripped thereon. Alternatively, only part of the effluent containing a peak component may be dripped on a different position of the ceramic substrate 32 in relation to detection of the peak by the detector 36. Although no IR chromatogram is obtained in this case, unwanted portions between the peaks can be discarded in order to effectively reduce the size of the ceramic substrate 32.

In the samples for infrared spectrometry obtained according to the LC/IR measuring method, spots of sample components are unspreadingly transferred onto the infrared-nonabsorbent substance powder layer, while the same are concentrated along the surface direction of the infrared-nonabsorbent substance powder layer. Thus, infrared spectrometry can be performed in high sensitivity.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A transfer method comprising the steps of placing a thin Layer Chromatography (TLC) plate having sample spots and including no support material on a porous substrate, placing a layer of an infrared-nonabsorbent substance on said TLC plate to be in close contact therewith, and upwardly moving a solvent from said porous substrate toward said infrared-nonabsorbent substance layer through said TLC plate by capillary action for vaporizing the same from the surface of said infrared-nonabsorbent substance layer, thereby transferring said sample spots developed in said TLC plate onto said infrared-nonabsorbent substance layer.

2. A transfer method in accordance with claim 1, wherein said infrared-nonabsorbent substance layer is a ceramic sheet.

3. A transfer method in accordance with claim 1, wherein said porous substrate is formed by a detachable pair of lower and upper substrates, said TLC plate is a flexible plate and said infrared-nonabsorbent substance layer is a powder layer, while said TLC plate is first placed on said upper substrate and then said infrared-nonabsorbent substance powder layer is formed on said TLC plate.

4. A transfer method in accordance with claim 3, wherein said porous substrate is a ceramic substrate.

5. A transfer method in accordance with claim 3, wherein said infrared-nonabsorbent substance layer is a KBr powder layer.

6. A transfer method in accordance with claim 3, wherein said infrared-nonabsorbent substance layer is a KCl powder layer.

7. A Liquid Chromatography/Infrared (LC/IR) measuring method, comprising the steps of:
   dripping an effluent for liquid chromatography on a porous substrate for vaporizing an eluant, thereafter forming a layer of infrared-nonabsorbent substance powder on said porous substrate; and
   upwardly moving a solvent through said porous substrate to said infrared-nonabsorbent substance powder layer by capillary action for vaporizing the same from the surface of said infrared-nonabsorbent substance layer, thereby transferring sample components adsorbed by said porous substrate to said infrared-nonabsorbent powder layer for preparing samples for infrared spectrometry.

8. An LC/IR measuring method in accordance with claim 7, wherein said porous substrate is a ceramic substrate.

9. An LC/IR measuring method in accordance with claim 7, wherein said infrared-nonabsorbent substance powder layer is a KBr powder layer.

10. An LC/IR measuring method in accordance with claim 7, wherein said infrared-nonabsorbent substance powder layer is a KCl powder layer.

11. An LC/IR measuring method in accordance with claim 7, wherein a position of said porous substrate for receiving said effluent for liquid chromatography is relatively moved at a constant speed with respect to an elution port.

12. An LC/IR measuring method in accordance with claim 7, wherein only part of said effluent for liquid chromatography containing a peak component is dripped on a different position of said porous substrate.

* * * * *